US012749575B2

(12) United States Patent
Gegner et al.

(10) Patent No.: US 12,749,575 B2
(45) Date of Patent: Sep. 29, 2026

(54) PROVIDING A VISUAL REPRESENTATION OF PATIENT MONITORING DATA FROM A PLURALITY OF PATIENT MONITORS

(71) Applicant: KONINKLIJKE PHILIPS N.V., Eindhoven (NL)

(72) Inventors: Guenter Gegner, Tuebingen (DE); Harald Greiner, Nufringen (DE); Jurgen Fischbach, Bondorf (DE)

(73) Assignee: KONINKKLIJKE PHILIPS N.V., Eindhoven (NL)

( * ) Notice: Subject to any disclaimer, the term of this patent is extended or adjusted under 35 U.S.C. 154(b) by 408 days.

(21) Appl. No.: 17/767,648

(22) PCT Filed: Sep. 30, 2020

(86) PCT No.: PCT/EP2020/077409

§ 371 (c)(1),
(2) Date: Apr. 8, 2022

(87) PCT Pub. No.: WO2021/069279

PCT Pub. Date: Apr. 15, 2021

(65) Prior Publication Data

US 2024/0079127 A1 Mar. 7, 2024

(30) Foreign Application Priority Data

Oct. 9, 2019 (EP) .................................... 19202210

(51) Int. Cl.
*G16H 40/67* (2018.01)

(52) U.S. Cl.
CPC .................................. *G16H 40/67* (2018.01)

(58) Field of Classification Search
CPC ............................................... G06Q 50/20–26
See application file for complete search history.

(56) References Cited

U.S. PATENT DOCUMENTS

2011/0105854 A1* 5/2011 Kiani ...................... G16Z 99/00 600/300
2011/0110572 A1* 5/2011 Guehring ............. A61B 6/5258 382/128
2018/0082035 A1* 3/2018 Collette ................. G16H 40/67
2018/0317826 A1* 11/2018 Muhsin .............. A61B 5/14552
2022/0338737 A1* 10/2022 Freeman .............. A61B 5/0077

OTHER PUBLICATIONS

International Search Report for PCT/EP2020/077409 Filed Sep. 30, 2020 and Dated Nov. 25, 2020.
Warren, I et al.: "Odintelehealth: A Mobile Service Platform for Telehealth", Procedia Computer Science, vol. 5, 2011, pp. 681-688.
https://en.wikipedia.org/wiki/Watchdog_timer.

* cited by examiner

*Primary Examiner* — Neal Sereboff

(57) ABSTRACT

A user interface for a patient monitoring system which is capable of providing a visual representation of patient monitoring data generated by a plurality of different patient monitors. The user interface bi-directionally communicates with the patient monitors in order to obtain the patient monitoring data. Embodiments also provide a patient monitoring system comprising a plurality of patient monitors and at least one user interface for displaying the patient monitoring data generated by said patient monitors. The user interface monitors its own status and provides an output indicating this status.

11 Claims, 4 Drawing Sheets

PROVIDING A VISUAL REPRESENTATION OF PATIENT MONITORING DATA FROM A PLURALITY OF PATIENT MONITORS

CROSS-REFERENCE TO PRIOR APPLICATIONS

This application is the U.S. National Phase application under 35 U.S.C. § 371 of International Application No. PCT/EP2020/077409, filed on Sep. 30, 2020, which claims the benefit of European Application No. 19292219.1 filed on Oct. 9, 2019. These applications are hereby incorporated by reference herein.

FIELD OF THE INVENTION

The present invention relates to the field of patient monitoring, and in particular to the handling of patient monitoring data.

BACKGROUND OF THE INVENTION

In a clinical setting, such as in an intensive care unit or neonatal intensive care unit, patient monitors are routinely used to autonomously monitor physiological data of subjects or patients. A patient monitor may be adapted to generate patient monitoring data, which may comprise the physiological data and/or data derived therefrom.

It is somewhat common for a patient monitor to generate alarm data, which indicates whether an alarm event has occurred, an alarm event being an indication that a patient or the patient monitor has entered a non-desirable state. For example, an alarm event may indicate a low heart-rate or $SpO_2$ level of the subject a low battery level or malfunction of the patient monitor.

Typically, a visual representation of the patient monitoring data (and alarm data in particular) is provided by the patient monitor by a two-dimensional screen directly connected via a wire or other electrical connection to the remainder of the patient monitor, e.g. via a Video Graphics Array (VGA) cable.

It is also known to provide or utilize additional user interfaces, such as a tablet or mobile phone, which receive updates from the patient monitor over a wired or channel. These user interfaces supplement the two-dimensional screen of the patient monitor by mirroring the visual representation and/or providing additional information about the patient monitoring data. Generally, these user interfaces operate by the patient monitor pushing patient monitoring data updates to the user interface.

There is an ongoing desire to increase the flexibility and usability of a patient monitoring system. There is also a desire to reduce the number of alarms or alerts provided to a caregiver/clinician.

SUMMARY OF THE INVENTION

The invention is defined by the claims.

According to examples in accordance with an aspect of the invention, there is provided a user interface for a patient monitoring system. The user interface is adapted to display a visual representation of patient monitoring data generated by a plurality of patient monitors that are each adapted to monitor a different patient.

The user interface comprises: a communication module adapted to communicate bi-directionally with two or more patient monitors over respective communication pathways to receive, from each patient monitor, patient monitoring data generated by the respective patient monitor; an output module for providing a user-perceptible output, the output module comprising coupleable to a two-dimensional display screen for generating a visual output; a user interface processor adapted to: obtain, from the communications module, the patient monitoring data received from each patient monitor; and control the two-dimensional display screen to provide a visual representation of the patient monitoring data generated by each patient monitor in communication with the user interface monitor a status of the user interface as well as a status of the display it is coupled to; and control the output module to provide a user-perceptible output indicating the status of the user interface. The communication module is adapted to communicate with at least one other user interface; the user interface further is adapted to use the communication module to receive patient monitoring data from at least one other user interface; and the user interface processor is adapted to control the two-dimensional display screen to be capable of further providing a visual representation of the patient monitoring data obtained from the at least one other user interface.

The present invention thereby provides a user interface that can reliably provide a visual representation of patient monitoring data generated by more than one patient monitor. This means that a reduced number of user interfaces and/or screens are required in order to provide the patient monitoring data of multiple patient monitors, thereby reducing cost.

The proposed user interface can also obtain patient monitoring data from a patient monitor with which the user interface is unable to communicate. That is, the proposed user interface can be passed patient monitoring data from another user interface. The patient monitoring data passed to the user interface from another interface may comprise patient monitoring data received from yet another user interface. Thus, patient monitoring data may be sent in a chain originating at a patient monitor and terminating at the user interface (with one or more other user interfaces forwarding the patient monitoring data along the chain).

Enabling a user interface to display patient monitoring data from multiple patient monitors also enables an increased flexibility of the patient monitoring system, allowing for new configurations of the patient monitors and the visual representation (e.g. enabling a visual representation to be provided in a separate room to the patient monitor).

A bidirectional communication between the user interface and the patient monitor enables a reliable connection to be set up, thereby avoiding the need for the patient monitor to comprise or be otherwise hardwired to a screen via a trusted wired connection for displaying a visual representation, whilst ensuring that the patient monitoring data is still available for viewing by a clinician. In other words, a potentially unreliable communication pathway, e.g. a communication pathway or a communication pathway that is at least partially outside the control of the operator of the patient monitoring system, can be used.

Monitoring, and displaying, a status of the user interface means that a failure in the user interface can be notified to the clinician/user. This ensures that the user interface can be made "reliable", in the sense that failures can be notified to the user, to encourage them to manually check the patient or the patient monitor, thereby avoiding the patient or patient monitor entering an undesirable state without the clinician noticing.

In some embodiments, the communication module is further adapted to monitor a status of the communication pathways between each patient monitor and the user interface; and the user interface processor is adapted to control the output module to provide a user-perceptible output indicating the status of the communication pathways between each patient monitor and the user interface.

Monitoring the status of the communication pathway ensures that the communication between the patient monitor(s) and the user interface is reliable. In particular, a clinician may be able to respond to a failure in the communication pathway, e.g. manually attending to the patient. Providing a user-perceptible output of the status of the communication pathway thereby reduces the risk that the patient will enter a clinically undesirable state unnoticed (e.g. as may be the case if the user interface simply acted upon patient monitoring data pushed to the user interface, without checking the status of the connection).

In some embodiments, the communication module is adapted to monitor a status of each communication pathway between a respective patient monitor and the user interface and/or a status of each patient monitor; and the user interface processor is adapted to control the output module to provide a user-perceptible output indicating the status of each communication pathway between a respective patient monitor and the user interface and/or each patient monitor.

Optionally, the communication module is adapted to communicate with at least one user interface; and the user interface is adapted to use the communication module to transmit patient monitoring data, received from one or more patient monitors, to at least one other user interface.

Thus, patient monitoring data may be shared between different user interfaces. This increases a flexibility of the overall patient monitoring system as, for example, user interfaces may be able to display a visual representation of patient monitoring data for patient monitors out of its own range. This approach also provides a number of fall back positions for failures in communication pathways, as herein described and explained.

Optionally, the communication module is adapted to monitor a status of a communication pathway between the user interface and each other user interface; and the user interface processor is adapted to control the output module to provide a user-perceptible output indicating the status of each communication pathway between the said user interface and each other user interface.

In another embodiment the user interface further includes a two-dimensional display screen being a part of the output module, for example.

According to examples in accordance with an aspect of the invention, there is provided a patient monitoring system comprising any herein described user interface according and a plurality of patient monitors each adapted to: generate patient monitoring data responsive to physiological data of a respective patient; and transmit the generated patient monitoring data to the user interface over a communication pathway.

In embodiments, each patient monitor is adapted to: monitor the status of the communication pathway between the patient monitor and the user interface; and in response to the monitored status indicating that the communication pathway, between the patient monitor and the user interface, is unable to successfully carry the patient monitoring data to the user interface, initiating transmission of the patient monitoring data to a different user interface over a different communication pathway.

In embodiments, each patient monitor further comprises an audible output module, wherein the patient monitor processor is adapted to, in response to the monitored status indicating that the communication pathway, between the patient monitor and the user interface, is able to successfully carry the patient monitoring data to a user interface, prevent the audible output module from generating any audible outputs responsive to the patient monitoring data.

Optionally, each patient monitor further comprises an audible output module, wherein the patient monitor processor is adapted to, in response to the monitored status indicating that the communication pathway, between the patient monitor and the user interface, is unable to successfully carry the patient monitoring data to a user interface, control the audible output module to provide a first audible output responsive to the patient monitoring data.

In embodiments, each patient monitor further comprises an audible output module, wherein the patient monitor processor is adapted to, in response to the monitored status indicating that the communication pathway, between the patient monitor and the user interface, is unable to successfully carry the patient monitoring data to a user interface, control the audible output module to provide a second audible output indicating a failure of the communication pathway.

Each patient monitor is preferably devoid of any two-dimensional screens for providing a visual representation of the patient monitoring data and/or is optionally configured to be unable to communicate with a device having a two-dimensional screen over a wired communication pathway.

According to an aspect of the invention, there is provided a method of controlling a user interface, comprising an output module coupleable to a two-dimensional screen, to display a visual representation of patient monitoring data generated by a plurality of patient monitors.

The method comprises: communicating bi-directionally with two or more patient monitors over respective communication pathways to receive, from each patient monitor, patient monitoring data generated by the respective patient monitor; controlling the two-dimensional display screen of the output module to provide a visual representation of the patient monitoring data generated by each patient monitor in communication with the user interface; monitoring a status of the user interface and the two-dimensional display screen; and controlling the output module to provide a user-perceptible output indicating the status of the user interface.

The method further comprises communicating with at least one other user interface to receive patient monitoring data obtained by the at least one other user interface; and controlling the two-dimensional display screen to further provide a visual representation of the patient monitoring data obtained from the at least one other user interface.

According to examples in accordance with an aspect of the invention, there is provided a computer program comprising code means for implementing any herein described method when said program is run on a processing system.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
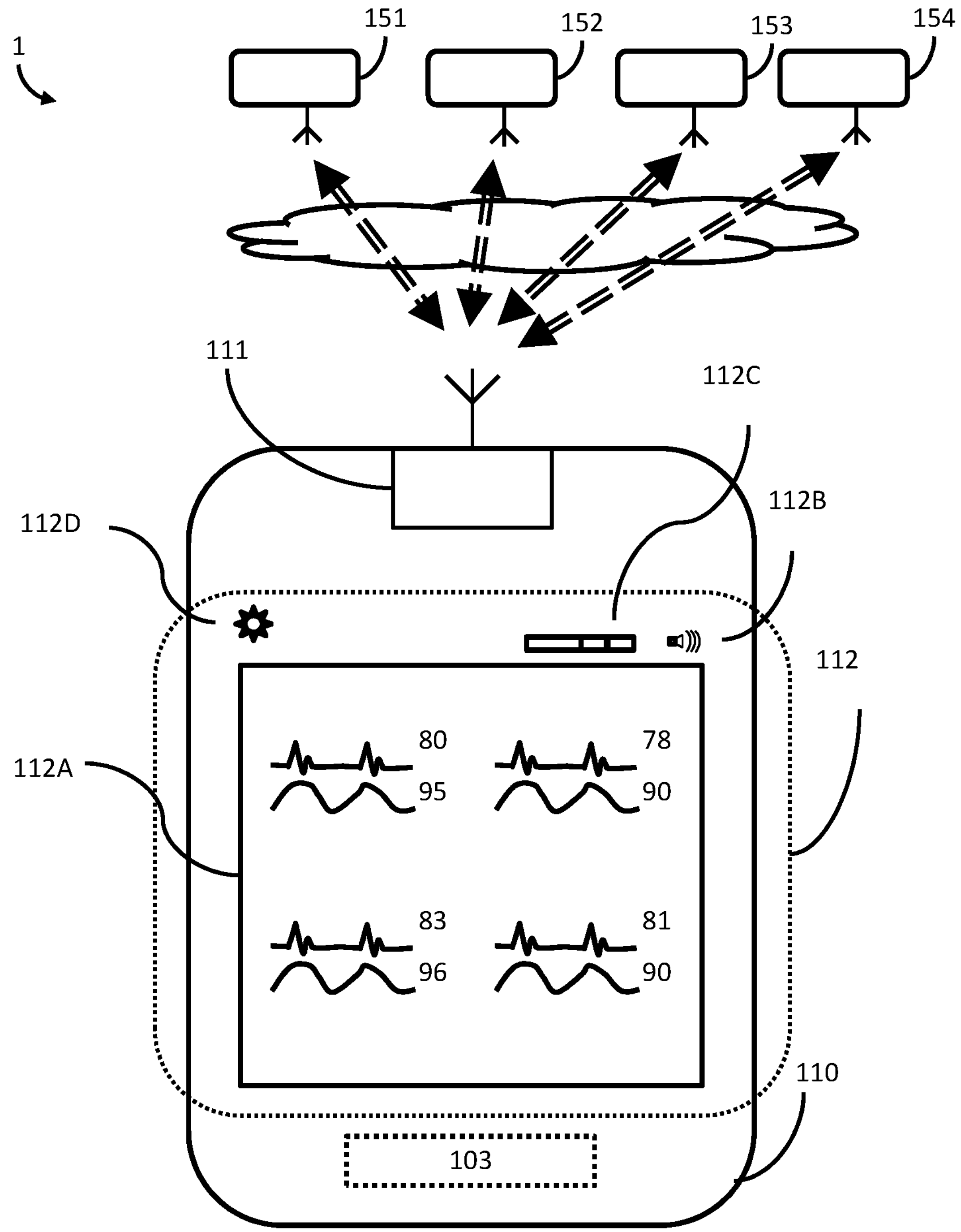
FIG. 1 illustrates a patient monitoring system according to an embodiment of the invention.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a user interface for a patient monitoring system that is capable of providing a visual representation of patient monitoring data generated by a plurality of different patient monitors. The user interface bi-directionally communicates with the patient monitors in order to obtain the patient monitoring data. Embodiments also provide a patient monitoring system comprising a plurality of patient monitors and at least one user interface for displaying the patient monitoring data generated by said patient monitors. The user interface monitors its own status and provides an output indicating this status.

Embodiments may be employed in clinical environments in which patients are being monitored by respective patient monitors, to provide a more flexible clinical environment.

FIG. 1 illustrates a patient monitoring system 1 comprising a user interface 110 and a plurality of monitors 151-154, according to a first embodiment of the invention. Of course, the user interface 110 itself demonstrates an embodiment of the invention, as does the overall patient monitoring system 1.

The user interface comprises 110 comprises a communication module 111, an output module 112, preferably comprising a two-dimensional display screen 112A, and at least a user interface processor 113. The user interface 110 is adapted to provide a visual representation of patient monitoring data obtained by two or more patient monitors.

Though the output module is illustrated as having a display screen 112A being an integral part of said module, it shall be understood by a skilled in the art person that the user interface 110 comprising the output module 112 can be in form of a separate unit and be coupled to an external display screen.

Each patient monitor 151-154 is adapted to monitor one or more physiological characteristics of the patient and generate patient monitoring data, to be visually represented by the user interface. The generated patient monitoring data is transmitted, by each patient monitor 151-154, to a user interface via respective communication pathways. A more detailed description of an example patient monitor is provided later.

For the sake of clarity, the patient monitoring data generated by a single patient monitor may be referred to as "an instance of patient monitoring data" or a "portion of patient monitoring data". This helps distinguish the patient monitoring data generated by different patient monitors from one another when appropriate.

Thus, the user interface 110 communicates with a plurality of patient monitors, which may form a "first set" of patient monitors. In the illustrated example, four patient monitors 151-154 each transmit patient monitoring data to the user interface 110 using respective communication pathways.

In particular, the communication module 111 of the user interface 110 is adapted to receive communications (comprising patient monitoring data) from each patient monitor of the first set 151-154.

Communications between the user interface 110 and the patient monitors 151-154 are bi-directional, i.e. the user interface is able to provide an input to each connected patient monitor and vice versa.

Communications over the communication pathway, between the patient monitor and the user interface, may be encoded or formatted using the medical device data language (MDDL) or by establishing a Transmission Control Protocol (TCP) link between the patient monitor and the user interface. Other suitable methods of encoding or formatting data would be apparent to the skilled person.

In preferable embodiments, the communication pathway is a wireless communication pathway, so that communications between the user interface and the patient monitor(s) are wireless.

A communication is considered to be wireless if at least part (e.g. some or all) of a communication pathway (over which the communication takes place) between the patient monitor and the user interface takes place over a wireless channel.

Any suitable wireless communication protocols or technologies may be used. Suitable wireless communication protocols that the patient monitor and user interface may use to communicate include an infrared link, Zigbee, Bluetooth, a wireless local area network protocol such as in accordance with the IEEE 802.11 standards, a 2G, 3G or 4G telecommunication protocol, and so on. Other formats will be readily apparent to the person skilled in the art.

When wireless communications are used, it is preferable for the wireless communication pathway to provide a direct communication link between the patient monitor and the user interface, e.g. using a near-field communication (NFC), Bluetooth or ZigBee protocol. In other embodiments, the wireless communication pathway is a personal or local area network such as those that can be established using WiFi technology (but does not comprise a wide area network). In yet other embodiments, the wireless communication pathway comprises a wide area network, e.g. the internet.

Communications, from the patient monitors 151-154 to the user interface 110, include patient monitoring data generated by the patient monitor (examples of which will be given later). Such communications may thereby enable the patient monitors 151-154 to effectively stream patient monitoring data to the user interface.

The (user interface processor 113 of the) user interface 110 obtains the patient monitoring data from each connected patient monitor 151-154 and controls the screen 112A to display a visual representation of the patient monitoring data obtained from each device (in the form of waveforms and/or numerical representation, for example). One example of a suitable visual representation is illustrated in FIG. 1.

In this way, a visual representation of different instances/portions of patient monitoring data is displayed by the display screen. Thus, patient monitoring data for a plurality of different patients can be displayed on a same display screen. This reduces the number of user interfaces that are required to provide a visual representation of patient monitoring data of multiple different patients, thereby reducing cost.

Various different methods of displaying a plurality of different instances of patient monitoring data will be apparent to the skilled person.

For example, each instance of patient monitoring data may be presented in its own window within the overall visual representation. Thus, each patient monitor (and therefore patient) may be associated with a different portion of the overall visual representation displayed by the user interface. This embodiment is illustrated in FIG. 1, in which each of the four patient monitors 151-154 communicating with the user interface 110 are associated with a different quadrant of the visual representation of the patient monitoring data displayed on the screen 112A.

As another example, in the visual representation, patient monitoring data for a first patient may overlap with patient monitoring data for a second patient (e.g. for comparison purposes). This may comprise, for example, plotting physiological data for different patients against a common axis.

In some examples, the output module 112 further comprises a speaker 112B for generating an audio output. The processor 113 of the user interface 110 may control the speaker 112B responsive to the patient monitoring data (although the speaker may instead or additionally be used for other purposes, set out below). Of course, the speaker may be controlled via an I2S interface, digital audio path, digital-to-analog converter (DAC), amplifier and so forth.

The present invention allows any device having a display screen as well as a speaker to become an active device for alarm management of a plurality of patients as long the user interface assures a reliable functionality of the separate units it is coupled to such as either a display and/or speaker. This is achieved by the user interface including its status check a step of checking the status of the unit it is coupled to. The advantage of the present solution is enabling any display screen with the user interface functionality. Normally, display screens of the patient monitors need to comply with strict medical requirements, wherein their visualization capabilities (contrast, active pixels, etc.) need to be operational 24/7 for months if not years. This requirement drives a prize of the patient monitoring system. The present invention advantageously provides an alternative solution, which allows rather than imposing the strict requirement on the display screen, wherein the physiological data are monitored to provide the user interface with the self check status functionality. This self check status functionality also includes monitoring of the display's visual performance, which informs the user as soon the display's quality degrades below the medically imposed threshold.

The patient monitoring data is responsive to at least physiological data of the patient monitored by the respective patient monitor, but may also be responsive to other parameters or variables. Methods of generating patient monitoring data by the patient monitor would be well known to the skilled person, examples of which will be described in more detail later.

The patient monitoring data may also comprise data responsive to a status of the patient monitor and/or any patient sensors in communication with the patient monitor. For example, the patient monitoring data may comprise an indication of whether or not an electrode (e.g. for monitoring a heart rate) is in electrical contact with a patient.

The patient monitoring data may comprise alarm data that indicates the occurrence or presence of alarm events.

As previously explained, an alarm event is an indication that a patient or the patient monitor has entered a non-desirable state. For example, an alarm event may indicate a low heart-rate or $SpO_2$ level of the subject a low battery level, a disconnected lead or a malfunction of the patient monitor. In particular, an alarm event may occur if a measured level of a physiological parameter cross a predetermined threshold (e.g. goes above a maximum threshold or goes below a minimum threshold).

Methods of generating alarm data would be readily apparent to the skilled person, examples of which will be described later.

In such examples, the user interface may display a visual representation of an alert (e.g. selectively display a red light or an alert symbol such as an exclamation mark) on the screen 112A when an alarm event is detected in any instances/portions of the patient monitoring data. In embodiments in which the user interface comprises a speaker 112B for generating an audio output, the processor may control the speaker to generate an audio alert responsive to an alarm event (e.g. a rapid beeping or continuous beep if an alarm event occurs or silence if no alarm event occurs). The visual/audio alert may contain information about the trigger for the alarm (e.g. identify the patient and/or physiological parameter that triggered the alarm).

In some examples, the output module 112 further comprises a dedicated alarm light output 112C, which may visually indicate the occurrence of an alarm event (i.e. separately from the screen 112A), to aid in providing a distinguishing identification of an alarm event.

The patient monitoring data, generated by each patient monitor, is formatted so that it is suitable for being handled by the user interface processor so that a visual representation of the patient monitoring data can be provided.

For example, the patient monitoring data may be formatted as raw data (e.g. raw physiological data or raw alarm events) for being processed into a visual representation by the user interface processor. In such embodiments, the user interface may be adapted to receive patient monitoring data from each patient monitor and generate display data for controlling the two-dimensional screen to provide a visual representation of the patient monitoring data of each patient monitor.

In other examples, the patient monitoring data may be formatted as display data (being data that defines a visual representation on a two-dimensional display screen). This allows each patient monitor to control the appearance of the (portion of the) visual representation of the instance of the patient monitoring data provided by the user interface on its screen. This reduces a processing power required by the user interface.

In this way, each patient monitor controls or defines the visual representation displayed by the screen of the user interface 110, so that the visual representation provides information on the patient monitoring data of the patient monitors 151-154.

Using a single user interface to provide a visual representation of patient monitoring data obtained from more than one patient monitor reduces the number of user interfaces required to monitor a subject. It also increases a flexibility of the overall patient monitoring system, e.g. by allowing user interfaces to be taken offline (as their responsibility could be taken over by another user interface) for repair and/or recharging.

Using a user interface to provide a visual representation of patient monitoring data in this manner also removes a need for the patient monitor itself to provide such a visual representation. Patient monitors can thereby be provided without potentially expensive or temperamental screens.

The user interface is also adapted to monitor its own status (i.e. the status of itself). In this way, the user interface is adapted to independently monitor its own functionality (e.g. checking battery levels, software errors, output module status and the like).

Methods of monitoring a status of, i.e. detecting the occurrence of errors within, an electronic device (such as the user interface) are well known to the skilled person.

In particular examples, the user interface may use a software and/or hardware watchdog, such as a watchdog timer, to monitor the status of itself. A watchdog operates so that it can be guaranteed that an indication of a status can be provided. In particular, the presence or absence of errors can be detected. A watchdog thereby ensures that the user interface is reliable. In particular, a watchdog may operate in a “fail-safe” mode, so that failure of a system or electronic device can be noticed by an operator of the user interface.

Some methods of monitoring a status of the user interface 110 may comprise monitoring the status of the output module 112, e.g. a speaker or audible output module. Failure of an output module may indicate a failure of the electronic device.

In an example in which the output module 112 comprises a speaker or audible output module, one status monitoring method may comprise controlling the speaker or audible output module to provide an inaudible test signal, and using a measuring circuit to obtain a magnitude of the signal at the test signal frequency. This magnitude can be used to gain knowledge about the functionality/status of the speaker or audible output module and its electrical connection to the host device (i.e. the user interface or the patient monitor).

For example, the measuring circuit may be adapted to measure an alternating current in a signal path of the audible output module. This allows easy measurement of the test signal in the circuit of the audible output module, e.g., by a shunt resistor. Alternatively, the audible output may be measured by other means e.g. with a microphone or an optical sensor or indirectly by measuring the supply current of the audible output module.

This enables the status of the speaker or audible output module to be accurately assessed, potentially forming an aspect of monitoring the status of the overall user interface or patient monitor.

In some examples, the inaudible test signal may be added on top of the normal audio signal of the speaker or audible output module. In this way, the normal audio signal is not affected and the environment is not disturbed by the inaudible test signal.

The skilled person would appreciate that other output modules may be monitored in a similar manner when monitoring a status of the user interface or patient monitor. For example, monitoring an output module may comprise monitoring a voltage drop across the output module (e.g. to detect if the output module has been short-circuited).

The user interface 100 is adapted to control the output module responsive to the determined status of itself (the user interface). In particular, a user-perceptible output maybe controlled based upon the determined status of the user interface.

Indicating the status of the user interface 100 may comprise, for example, providing no user-perceptible output if the user interface has completely failed (e.g. lost power), providing a first user-perceptible output (e.g. a green light or no audible sound) if no errors are detected and/or providing a second user-perceptible output (e.g. a red light or an audible sound) if at least one error is detected.

The controlled user-perceptible output may depend upon the available elements of the output module. For example, if the output module comprises a speaker, the user-perceptible output may provide different audible outputs (or absence of audible outputs) depending upon the status of the user interface.

The user interface 110 may be adapted to independently monitor the status of each communication pathway between the user interface 110 and a respective patient monitor 150.

In particular, it may be adapted to independently determine whether or not each communication pathway has failed and/or whether or not the communication pathway is incapable of successfully carrying/streaming the patient monitoring data from the respective patient monitor. In other words, they each determine whether each communication pathway is sufficiently stable to carry patient monitoring data from a patient monitor. Failure to carry this information may be due to, for example, the user interface 110 going out of range (if the communication pathway is wireless), the user interface failing (e.g. running out of battery) or the communication pathway having saturated bandwidth, e.g. too much traffic/noise such as transmissions from other patient monitors within the same frequency band.

In preferred embodiments, the user interface may be adapted to determine whether each communication pathway is able to successfully carry the patient monitoring data from a patient monitor to the user interface within a predetermined time period, thereby determining the status of the communication pathway. The length of this predetermined time period is preferably no less than an allowable delay for generating a user-perceptible alarm in response to a non-desirable state of the patient, e.g. according to clinically acceptable guidelines. For example, the length of this predetermined time period may be in the region of 0.1 seconds to 3 seconds, for example from 0.1 seconds to 1 second.

The user interface 110 may also monitor the status of the communication pathway 190 using the communication module 111.

Methods of monitoring the status of a communication pathway would be known to the skilled person, and generally depend upon the type, structure, format or protocol of the communication pathway.

By way of a simple example, a status of a communication pathway may be checked by initiating a handshake protocol or “pinging” the other device in the communication pathway. A response from the other device may be checked (e.g. a lag in the communication pathway may be checked) and used to determine the status of the communication pathway.

In another example, a certain communication protocol may comprise transferring (a certain amount of) information at periodic intervals. The status of the communication may be checked by determining whether information has been received within the periodic interval, wherein a missed communication indicates a deterioration of the communication pathway, i.e. a change in status.

In yet another example, a communication protocol may comprise timestamping communications (e.g. from the patient monitor to the user interface or vice versa). The status of the communication pathway may be checked by determining whether a timestamped communication has been received within a predetermined period of time (since the timestamp), which may be the expected length of time for a communication to take place. Failure to receive the communication within the predetermined time period may indicate a deterioration of the communication pathway, i.e. a change in status.

The user interface 110 may be adapted to control one or more user-perceptible outputs (e.g. a visual, audible or haptic output) responsive to the independently determined status of the communication pathway. The user interface 110 may indicate the status using the output module 112, e.g. via the two-dimensional display screen 112A, the (optional) speaker 112B, a dedicated light output 112D (which forms an optional part of the output module 112).

Indicating the status of the module may comprise, for example, providing no user-perceptible output (e.g. no audible output or no visual representation) if the communication pathway is sufficiently stable to carry the patient monitoring data; and providing a user-perceptible output (e.g. an audible output or the presence of a certain visual representation) if the communication pathway is determined to not be sufficiently stable to carry the patient monitoring data.

In other words, at least one user-perceptible output is controlled responsive to the status of the communication pathway. Other methods of indicating a status, and suitable modules for providing a user-perceptible output of the same, would be apparent to the skilled person.

The user interface may be adapted to monitor a status of each patient interface with which is communicates.

Checking the status of a patient monitor may be performed according to any known method of monitoring the status of another device, e.g. employing heartbeat protocols or by iteratively requesting status information from the patient monitor. The user interface may be further adapted to provide a user-perceptible output responsive to the monitored status of the other device. The user interface may use the output module to provide this user-perceptible output. This improves a user's cognition of device failures.

Figure 2:
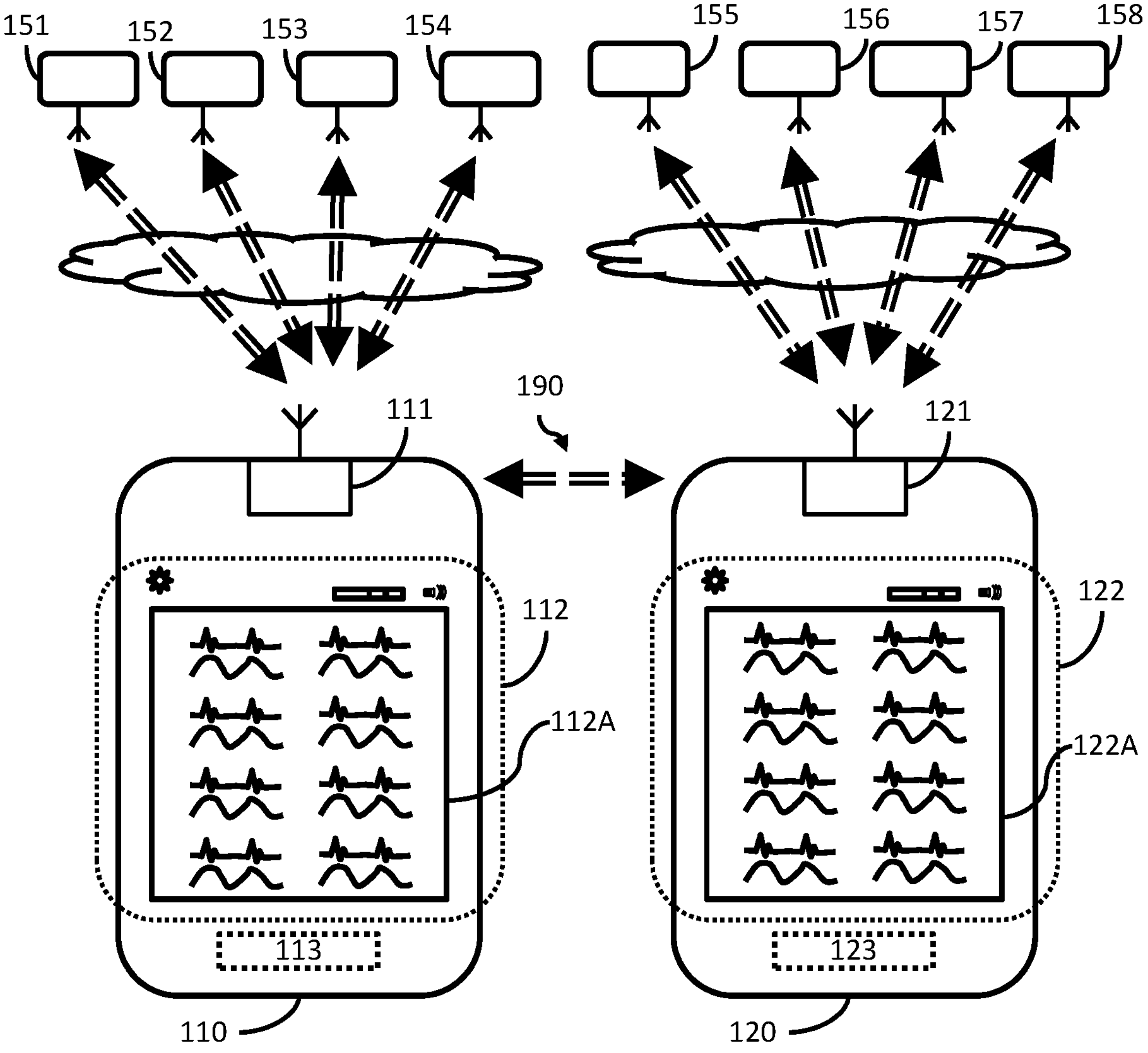
FIG. 2 illustrates a patient monitoring system according to another embodiment of the invention.

FIG. 2 illustrates a patient monitoring system 2 according to a second embodiment of the invention. The patient monitoring system 2 comprises a first user interface 110, a second user interface 120 and a plurality of patient monitor 151-158.

Each user interface 110, 120 operates in substantially the same way as the user interface of the first embodiment (illustrated in FIG. 1), with some additional functionality. Both the first 110 and second 120 user interfaces therefore comprise a communication module 111, 121, an output module 112, 122, comprising at least a two-dimensional display screen 112A, 122A, and a user interface processor 113, 123.

The first user interface 110 receives patient monitoring data from a first set of patient monitors 151-154. The second user interface 120 receives patient monitoring data from a second set of patient monitors 155-158.

The patient monitors 151-158 may be adapted to select with which user interface 110, 120 to communicate with based on, for example, a signal strength between the patient monitor and the user interface(s). In other examples, each patient monitor may be manually paired (e.g. using a key exchange mechanism) with a particular user interface.

The user interfaces 110, 120 are further adapted to communicate with one another, using their respective communication modules 111, 121, over another communication pathway 190. The communication pathway 190 may be embodied as any previously described communication pathway.

In particular, the user interfaces 110, 120 are each adapted to pass patient monitoring data to the other user interface, over the communication pathway. Thus, the first user interface 110 is adapted to transmit patient monitoring data to the second user interface 120 and vice versa. Similarly, the first user interface 110 is adapted to receive patient monitoring data from the second user interface 120, and vice versa.

The patient monitoring data passed by the user interfaces is preferably the patient monitoring data obtained by the respective user interfaces from the associated patient monitors, or at least responsive thereto. Of course, the patient monitoring data passed by the user interfaces may comprise patient monitoring data received from yet another user interface, or data responsive thereto. Thus, patient monitoring data may be sent in a chain originating at a patient monitor and terminating at a user interface (with one or more user interfaces forwarding the patient monitoring data along the chain).

In the illustrated example, the first user interface 110 passes (to the second user interface 120) patient monitoring data obtained/received from the first set of patient monitors 151-154 and the second user interface 120 passes (to the first user interface 110) patient monitoring data obtained/received from the second set of patient monitors 155-158.

The user interface processor 113, 123 of each user interface 110, 120 may be adapted to control their respective display screens 112A, 122A to further provide a visual representation of the patient monitoring data obtained from the other user interface 120, 110. Thus, the user interface processor 113, 123 is capable of controlling their display screen 112A, 122A to provide a visual representation of the patient monitoring data obtained from the other user interface 120, 110.

Thus, the visual representation displayed by the display screen 112A, 122A can be of the patient monitoring data generated by the patient monitors communicating with that user interface as well as the patient monitors communicating with the other user interface(s).

Thus, patient monitoring data may be shared between different user interfaces, so that the user interface is able to display a visual representation of patient monitoring data generated by patient monitors in communication with other user interfaces. This improves a flexibility of the overall patient monitoring system.

In some embodiments, each user interface 110, 120 may be adapted to monitor a status of the communication pathway(s) between itself and the other user interface(s). Methods of monitoring a status of a communication pathway have been previously described.

In some embodiments, each user interface 110, 120 may be adapted to monitor a status of each user interface 120, 110 with which it communicates. Methods of monitoring a status of another device have previously been described, in the context of the user interface monitoring a status of a patient monitor, and may be adapted for use here.

Each user interface processor may be adapted to control its own output module 112, 122 to provide a user-perceptible output indicating the status of each communication pathway 190 between the said user interface and each other user interface and/or a user-perceptible output indicating the status of each other user interface. Provision of the user-perceptible output(s) may be provided in a similar manner to the (optional) status of the communication pathway between a patient monitor and the user interface. For example, the user-perceptible output(s) may be provided via the two-dimensional display screen 112A, 122A, the (optional) speaker, and/or a dedicated light output (which forms an optional part of the output module 112, 122).

In this second embodiment, it has been described how each user interface may transmit and receive patient monitoring data. However, the skilled person will appreciate that different configurations of the user interface may be used to advantage so that, for example, a user interface may be adapted to only transmit (and not receive) patient monitoring data or vice versa.

In one example, a first user interface may receive patient monitoring data from patient monitors only, whereas a second user interface may receive patient monitoring data from the first user interface and from patient monitors.

In another example, a first user interface receives patient monitoring data from patient monitors and a second user interface; a second user interface receives patient monitoring data from patient monitors, a first user interface and a third user interface; and a third user interface receives patient monitoring data from patient monitors only.

Of course, it is not essential that all patient monitoring data received by a user interface (from another user interface) is visually represented by the screen. By way of example, some patient monitoring data may be forwarded to another user interface for display, e.g. if the other user interface is out of range of the relevant patient monitor or if too many patient monitors, e.g. >4 or >8, are sending patient monitoring data to that user interface.

It should be clear, however, that a visual representation of patient monitoring data transmitted by each patient monitor should be displayed by at least one user interface.

Some user interfaces may be configured to enable a user to select which patient monitoring data (of all received patient monitoring data) is visually represented by the screen.

Some user interface may be configured to enable a user to request additional patient monitoring data from other patient monitors or user interfaces. In response to such a request, the user interface may attempt to contact the other patient monitors and/or user interfaces in an effort to obtain such patient monitoring data.

The skilled person will appreciate that various configurations for a patient monitoring system can therefore be achieved in which patient monitoring data is shared between different user interfaces.

It has previously been described, with reference to the first embodiment, how a user interface may be adapted to monitor the status of itself, and optionally a status of a communication pathway between itself and each patient monitor and/or a status of each patient monitor with which it communicates.

It has also been described how a user interface may be adapted to monitor a status of a communication pathway between itself and each other user interface with which it communicates and/or a status of each user interface with which is communicates.

The user interface may be adapted to perform certain actions in response to any of these statuses indicating a failure or non-failure (i.e. whether the status indicates an "active" or "inactive" state), in itself, a communication pathway, patient monitor or other user interface.

For example, a user interface may be adapted to perform certain actions in response to determining that a communication pathway between itself and a patient monitor is unable to successfully carry patient monitoring data. In this example, these certain actions may comprise sending a request to another user interface 110 (e.g. over a communication pathway 190) for that other user interface to obtain and forward the patient monitoring data from the patient monitor with which the user interface 120 is unable to communicate.

Of course, the user interface may therefore be adapted to receive and act upon such a request from another user interface, e.g. by appropriating attempting to communicate with the indicated patient monitor. A similar process may be performed if a user is able to provide a request, to a user interface, for additional patient monitoring data.

In another example, the user interface may be adapted to respond to a detected failure in the status of another user interface (or the communication pathway thereto) by attempting to contact the patient monitors with which the user interface was previously communicating. This may ensure that the failure of a user interface (which would cause a failure in the communication pathway) does not result in the patient monitoring data of associated patient monitors no longer being displayed to a user.

Thus a more flexible patient monitoring system can be provided, that is responsive to failures within elements of the patient monitoring system.

A patient monitor may be similarly adapted to monitor a status of itself and/or a communication pathway and/or a user interface and react or respond to a change in the status. This further improves the flexibility and responsiveness of the patient monitoring system.

Figure 3:
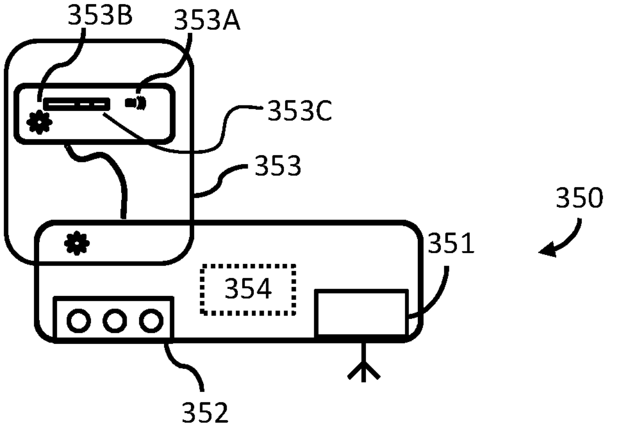
FIG. 3 illustrates a patient monitor for use in an embodiment of the invention.

To improve an understanding of such a possible patient monitoring system, various embodiments of and adaptations to patient monitors of a patient monitoring system will now be described with reference to FIG. 3. FIG. 3 illustrates an embodiment of a patient monitor 350, for use in the first or second embodiment of the patient monitoring system.

The patient monitor 350 comprises a communication system 351, an input module 352, a (optional) secondary alarm module 353 and a patient monitor processor 354. The patient monitor 350 is adapted to monitor one or more physiological characteristics of the patient and generate patient monitoring data for transmittal to a user interface.

The patient monitoring data is responsive to at least physiological data of the patient monitored by the respective patient monitor, but may also be responsive to other parameters or variables.

Some methods of generating patient monitoring data responsive to physiological data comprise receiving, at the input module 352 of the patient monitor, one or more physiological data streams from a patient sensor (such as a heart-rate monitor, a pulse oximeter and so on). The (processor 354 of the) patient monitor 350 is adapted to receive such information and generate patient monitoring data for display.

In some embodiments, the patient monitor may itself comprise one or more patient sensors for directly obtaining physiological data of the patient, e.g. comprise one or more of: a camera, a heart rate monitor, a respiration rate monitor, a pulse oximeter, a blood pressure monitor and so on. In other embodiments, these may be separate elements to the patient monitor.

The patient monitoring data may therefore comprise, for example, physiological information of the patient (e.g. heart rate, respiratory rate, $SpO_2$ level, temperature, urine output and so on). Physiological information may, for example, comprise information on any vital sign of the patient, any other sign/symptom of the patient or any other measureable quantity of the patient or of treatment devices provided to the patient (such as an amount left in an IV drip or a current battery level of a pacemaker).

The patient monitoring data may comprise alarm data that indicates the occurrence or presence of alarm events. This alarm data is preferably responsive to at least physiological data of the patient monitored by the patient monitor. In some embodiments, the alarm data is also responsive to a status of the patient monitor and/or sensors providing physiological data to the patient monitor.

In an example, alarm data is generated by comparing values of obtained physiological data to one or more predetermined thresholds. For example, alarm data may indicate the occurrence of an alarm event if a subject's heart rate (monitored by the patient monitor) falls below a first predetermined value or rises above a second predetermined value.

The patient monitor may be adapted to format the patient monitoring data so that it is suitable for (being processed for) being displayed by the screen of the user interface.

It has previously been described, with reference to the first embodiment, how a user interface may be adapted to monitor the status of each patient monitor and/or a communication pathway between itself and each patient monitor.

In some embodiments, each patient monitor is adapted to perform an analogous process of monitoring the status of the (or each) user interface and/or the communication pathway between itself and the user interface (which may use similar methods to those previously described with reference to the user interface). This may be performed by the communication system 351 of the patient monitor 350. The patient monitor may indicate the status(es) using the secondary alarm module 353 in a similar manner, which may provide one or more of a visual, audible or haptic output. Preferably, the secondary alarm module is, or comprises, a speaker, to avoid the need for the patient monitor to have a screen. Thus, the patient monitor may be devoid of a screen.

By way of example, the secondary alarm module may comprise a speaker 353A for generating an audible alert. In another example, the secondary alarm module 353 may comprise a dedicated visible output (e.g. a lamp) 353B for generating a visual alert.

The patient monitor may be adapted to perform certain actions in response to the monitored status(es) indicating that the user interface(s) has failed or that communication pathway is able or unable to carry or otherwise transmit the patient monitoring data to the user interface.

Accordingly, in some embodiments, the patient monitor is adapted to suppress/mute/prevent audible outputs in response to determining that the user interface is active and/or that the communication pathway is capable of carrying the patient monitoring data to a connected user interface. Thus, audible alarms can be suppressed at the patient monitor when the user interface is able to provide its own user-perceptible output on the data that would trigger the audible output.

In particular, the patient monitor may be adapted to suppress/mute/prevent audible outputs in response to determining that the user interface is active and/or that the communication pathway is capable of carrying the patient monitoring data to a connected user interface, wherein the patient monitoring data comprises alarm data.

Some clinical compliance guidelines necessitate the generation of an audible alarm in response to an alarm event (e.g. a patient's heartrate falling below a predetermined value).

In such scenarios, the patient monitor may be adapted to suppress audible outputs in response to determining that the user interface is active and/or that the communication pathway is capable of carrying the patient monitoring data (which comprises alarm data) and the user interface comprising a speaker adapted to provide an audible output responsive to the patient monitoring data. This enables the clinical compliance guidelines to be safely met, whilst reducing the number of audible alarms output by the patient monitor, i.e. in the vicinity of the patient.

Checking whether the user interface has a speaker may be performed, for example, by identifying a type or label of the user interface and/or sending a query to the user interface to query the existence of a speaker.

In other examples, the patient monitor may be adapted to suppress audible outputs for certain alarm events (e.g. non-critical alarm events), but not suppress audible outputs for other alarm events (e.g. critical alarm events), in response to determining that the user interface is active and/or that the communication pathway is capable of carrying the patient monitoring data (which comprises alarm data) and the user interface comprising a speaker adapted to provide an audible output responsive to the patient monitoring data. This provides a back-up option in the event that the condition of the patient rapidly deteriorates, whilst still enabling the overall number of alarms to be reduced.

These advantages enable more flexible use cases to be supported, such as enabling caregivers to be positioned in a separate (observation) room, whilst ensuring that patient monitoring data will either be provided to them or that they will be aware if there is a failure to provide the patient monitoring data.

The patient monitor may be adapted to monitor the status of itself. i.e. independently monitor its own functionality (e.g. checking battery levels, software errors, output module status and the like). Methods of monitoring a status of an electronic device have bene previously described in the context of a user interface.

The patient monitor may be adapted to perform certain actions in response to determining that there is a failure (or no failure) in the user interface(s), the communication pathway to the user interface(s) and/or the patient monitor itself. A couple of examples of such embodiments have been previously described, e.g. suppressing audible outputs or the like.

From the foregoing, it is clear that embodiments may enable the user interface(s) and/or the patient monitor(s) to monitor the status of communication pathways, other devices with which they communicate and/or themselves. This may include, for example, the user interface being able to monitor a status of themselves, at least one other user interface (and/or a communication pathway thereto) and/or a patient monitor (and/or a communication pathway thereto) and act in response to this determination. This may include, for example, the patient monitor being able to monitor a status of themselves and/or at least one user interface (and/or a communication pathway thereto), and act in response to this determination.

This approach enables flexibility in the overall patient monitoring system, by enabling different devices to respond to failures and/or non-failures of different elements of the patient monitoring system.

Figure 4:
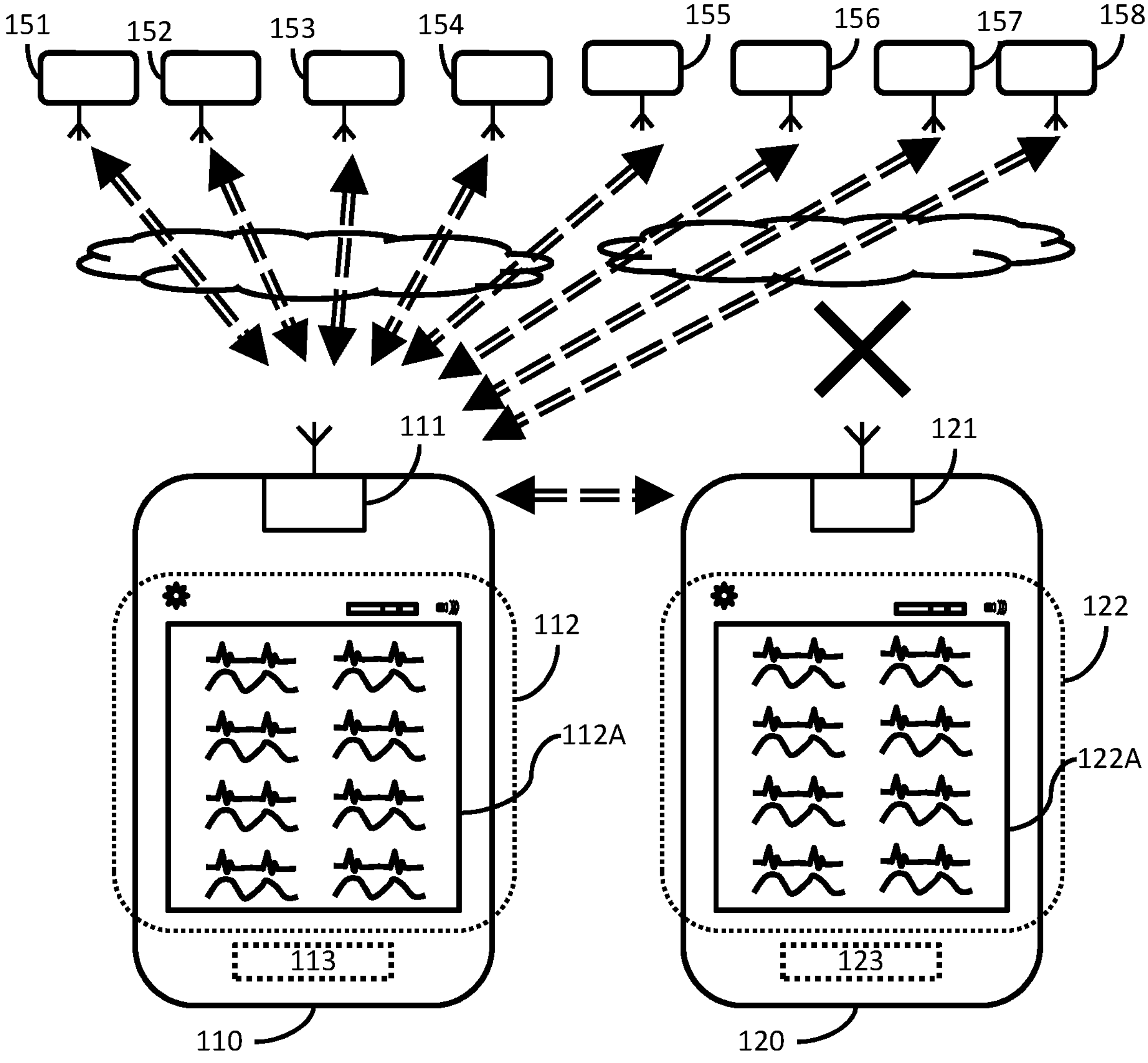
FIG. 4 illustrates a patient monitoring system according to an embodiment.

Some examples of this approach can be understood with reference to FIG. 4.

FIG. 4 illustrates a scenario for the second embodiment of the patient monitoring system 2, in which scenario the communication pathway between each of a second set of patient monitors 155-158 and the second user interface is unable to carry or otherwise transmit the patient monitoring data from each patient monitor to the second user interface.

This scenario may occur, for example, due to failure of the second user interface (e.g. a technical malfunction or the second user interface running out of battery) or the second user interface moving out of range (of a wireless communication pathway).

In response to determining that the communication pathway(s) is unable to successfully carry the patient monitoring data to the second user interface (or detecting that the second user interface itself has failed), a patient monitor 155-158 in the second set may attempt to contact another user interface 110, e.g. by setting up a new communication pathway to the other user interface. In the illustrated example, this other user interface is the first user interface 110.

Each patient monitor may be configured to know all active user interfaces, e.g. if the user interfaces advertise their services.

The patient monitors 155-158 may then transmit their patient monitoring data to the first user interface 110. The first user interface 110, in turn, receives the additional patient monitoring data from the second set of patient monitors 155-158.

This process may require a registration of the patient monitor on the first user interface 110. Methods of registering two devices together (e.g. pairing) are well known in the art. Registration on another user interface may take place in response to a failure of the user interface or a communication pathway thereto, or may be performed in advance (e.g. a patient monitor may be registered with multiple different user interface).

In some embodiments, the first user interface 110 is adapted to display a visual representation of the patient monitoring data received directly from the second set of patient monitors. This embodiment is illustrated in FIG. 4. This course of action can be taken even if the first user interface is unable to communicate with another user interface (e.g. if the user interface is not configured to be capable of communicating with another user interface or because it is unable to contact another user interface).

In other embodiments, the actions performed by the first user interface may depend upon whether the first user interface is able to communicate with another user interface, such as the second user interface. Thus, the actions may depend upon the monitored status of the communication pathway between the first user interface and each other user interface.

In one example, in response to the monitored status of the communication pathway between the first user interface 110 and the second user interface 120 indicating that the communication pathway is capable of carrying patient monitoring data, the first user interface 110 may forward the patient monitoring data (obtained from the second set of patient monitors) to the second user interface 120.

Of course, the first user interface 110 may also display a visual representation of this patient monitoring data (obtained from the second set) using its screen 112A. However, this is not essential if the data is successfully forwarded.

In response to the monitored status of the communication pathway between the first user interface 110 and the second user interface 120 indicating that the communication pathway is capable of carrying patient monitoring data, the first user interface 110 may simply display a visual representation of the patient monitoring data received from the second set of patient monitors.

Thus, the patient monitoring data of the second set of patient monitors 155-158 is displayed by at least one user interface, thereby ensuring that the patient monitoring data is available for review and monitoring by a clinician. This thereby avoids a patient entering a clinically undesirable state without being recognized by a clinician.

Preferably, the first user interface 110 is adapted to attempt forwarding the patient monitoring data from the second set of patient monitors to the second user interface in the first instance. The patient monitoring data from the second set of patient monitors may, for example, comprise an indication that it was originally intended for the second user interface (e.g. in header information), which may be processed by the first user interface. Of course, the patient monitor(s) may be adapted accordingly, to insert such indication(s).

If the patient monitor loses connection with the second user interface (i.e. the communication pathway fails), and is unable to contact another user interface, then the patient monitor may itself generate a user-perceptible output (e.g. using the secondary alarm module 353). This user-perceptible output may indicate a failure to connect to a user interface. In another embodiment, the user-perceptible output is responsive to the patient monitoring data, so that the patient monitor itself takes over the responsibility of alerting a clinician to the patient monitoring data.

It has been described how the patient monitor may be adapted to, if connection is lost with a user interface (e.g. the second user interface), begin contacting another user interface. In such embodiments, the patient monitor may be adapted to (in the background) monitor a connection to the original user interface to identify if the original user interface becomes contactable again. The patient monitor may then switch back to the original interface when/if it becomes available. Of course, the patient monitor may indicate to the other user interface that it will switch back to the original user interface.

Of course, any herein described patient monitor may be adapted to provide the patient monitoring data that it generates to more than one user interface or other device. By way of example only, the patient monitor may provide patient monitoring data to a central system or station.

The patient monitor(s) and/or user interface(s) may be adapted to communicate with one another to exchange information about what back-up means are available should a communication pathway or device fail (e.g. availability of another user interface to forward patient monitoring data, should a user interface fail). This allows the patient monitor (s) and/or user interface(s) to co-ordinate in the event of a failure of a device or communication pathway.

In some embodiments, each device controls its user-perceptible output based on the available back-up means. For example, failure of a patient monitor to communicate with a first user interface may not trigger an audible alarm (by the patient monitor) if another user interface is available as a back up, whereas failure to communicate with any user interface may trigger an audible alarm (by the patient monitor).

Figure 5:
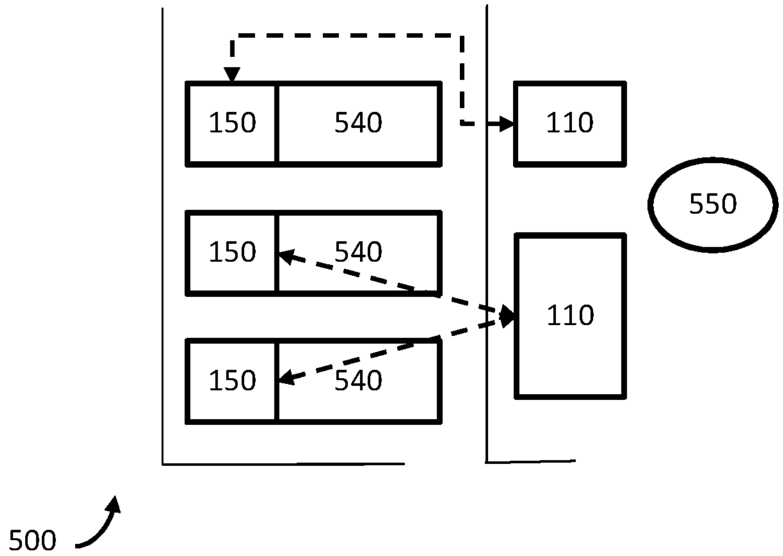
FIG. 5 illustrates a use-case scenario for a patient monitoring system according to an embodiment.

FIG. 5 illustrates a use case scenario for a patient monitoring system 500 according to an embodiment of the invention.

The patient monitoring system 500 comprises a plurality of different patient monitors 150 and a plurality of different user interfaces 110. In this illustrated scenario, a user interface is adapted to be capable of communicating with a plurality/set of different patient monitors, and each patient monitor is associated with a respective bed 540 (i.e. a specific patient).

The patient monitors 150 are positioned in a first room 505 (e.g. an intensive care unit). The user interface 110 are positioned in a second, separate room 506 (e.g. an observation room), to which clinician 250 can be assigned.

Each patient monitor 150 communicates with a user interface 110, as previously described. This enables patient monitoring data, such as alarm data, to be transmitted to be a separate room 505 to the room occupied by the patient monitors. In turn, this enables alarms or other user-perceptible outputs to be suppressed at each patient monitor 150 (as these alarms may instead be provided by the user interfaces), leading to a quieter first room 505. This can significantly reduce patient stress and/or alarm fatigue of a clinician present in the first room 505, whilst ensuring that appropriate data is still provided to a clinician 550 (present in the second room 505).

Thus, the proposed patient monitoring system can enable reduced patient stress and reduced alarm fatigue by reliably transferring patient monitoring data to a user interface, whilst ensuring that a failure to transfer patient monitoring data is notified to a user.

Of course, it will be appreciated that, in some embodiments, a user interface is operable in a mode in which is communicates with only a single patient monitor 150. This scenario is illustrated in FIG. 5. However, it will be clear that the user interfaces, according to embodiments of the invention, are capable of communicating with more than one patient monitor, and preferably also capable of communicating with one or more other user interfaces.

Figure 6:
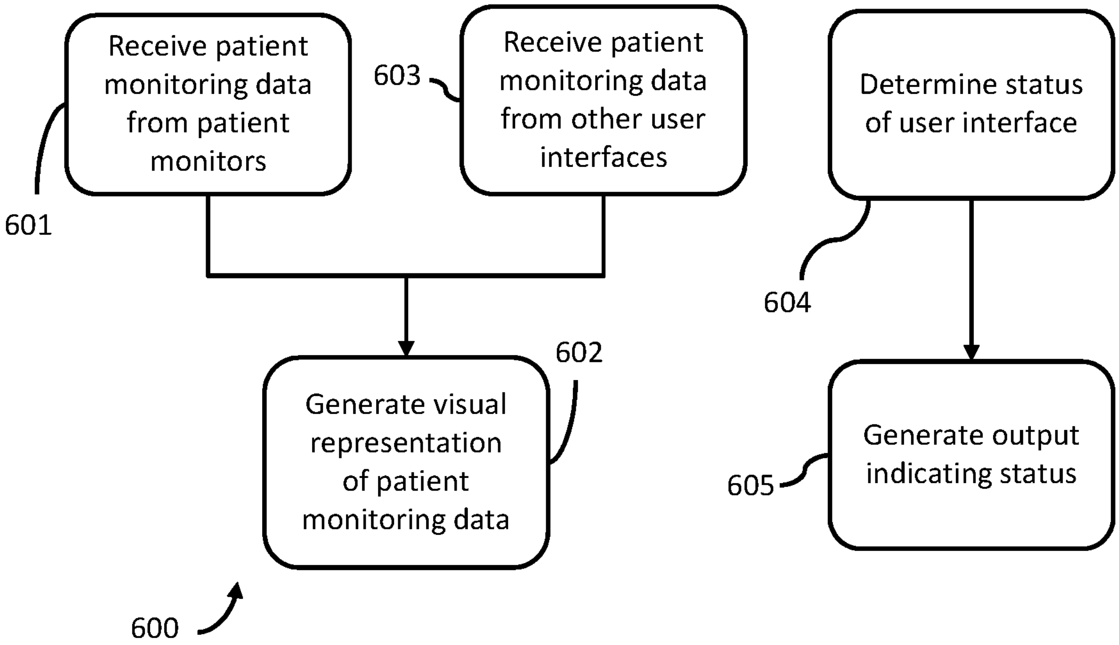
FIG. 6 illustrates a method according to an embodiment of the invention.

FIG. 6 illustrates a method 600 according to an embodiment of the invention.

The method 600 for controlling a user interface, comprising an output module having a two-dimensional screen, to display a visual representation of patient monitoring data generated by a plurality of patient monitors.

The method comprises a step 601 of communicating bi-directionally with two or more patient monitors over respective communication pathways to receive, from each patient monitor, patient monitoring data generated by the respective patient monitor.

The method further comprises a step 602 of controlling the two-dimensional display screen of the output module to provide a visual representation of the patient monitoring data generated by each patient monitor in communication with the user interface.

Optionally, the method may comprise a step 603 of communicating with at least one other user interface to receive patient monitoring data obtained by the at least one other user interface.

The step 602 may be adapted to comprise controlling the two-dimensional display screen to further provide a visual representation of the patient monitoring data obtained from the at least one other user interface.

The method 600 further comprises a step 604 of monitoring a status of the user interface; and a step 605 of controlling the output module to provide a user-perceptible output indicating the status of the user interface. Suitable examples of these steps have been previously described.

In any foregoing embodiments, it will be understood that the user interface is configured to be physically detached or detatachable from any patient monitor. In some embodiments, for example, the user interface may be attachable to the patient monitor for the purposes of charging, or when a clinician is attending to patient monitored by the patient monitor (to ensure more accurate and up-to-date patient monitoring information).

The skilled person would be readily capable of developing a processing system for carrying out any herein described method. Thus, each step of the flow chart may represent a different action performed by a processing system, and may be performed by a respective module of the processing system.

Embodiments may therefore make use of a processing system. The processing system can be implemented in numerous ways, with software and/or hardware, to perform the various functions required. A processor is one example of a processing system which employs one or more microprocessors that may be programmed using software (e.g., microcode) to perform the required functions. A processing system may however be implemented with or without employing a processor, and also may be implemented as a combination of dedicated hardware to perform some functions and a processor (e.g., one or more programmed microprocessors and associated circuitry) to perform other functions.

Examples of processing system components that may be employed in various embodiments of the present disclosure include, but are not limited to, conventional microprocessors, application specific integrated circuits (ASICs), and field-programmable gate arrays (FPGAs).

In various implementations, a processor or processing system may be associated with one or more storage media such as volatile and non-volatile computer memory such as RAM, PROM, EPROM, and EEPROM. The storage media may be encoded with one or more programs that, when executed on one or more processors and/or processing systems, perform the required functions. Various storage media may be fixed within a processor or processing system or may be transportable, such that the one or more programs stored thereon can be loaded into a processor or processing system.

It will be understood that disclosed methods are preferably computer-implemented methods. As such, there is also proposed the concept of computer program comprising code means for implementing any described method when said program is run on a processing system, such as a computer. Thus, different portions, lines or blocks of code of a computer program according to an embodiment may be executed by a processing system or computer to perform any herein described method. In some alternative implementations, the functions noted in the block diagram(s) or flow chart(s) may occur out of the order noted in the figures. For example, two blocks shown in succession may, in fact, be executed substantially concurrently, or the blocks may sometimes be executed in the reverse order, depending upon the functionality involved.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A user interface for a patient monitoring system, the user interface being adapted to display a visual representation of patient monitoring data generated by a plurality of patient monitors that are each adapted to monitor a different patient, the user interface comprising:

a communication module adapted to communicate bi-directionally through encoded medical device data language messages with two or more patient monitors of the plurality of patient monitors over respective communication pathways to receive, from each patient monitor, patient monitoring data generated by respective patient monitor of the plurality of patient monitors;

an output module for providing a user-perceptible output, the output module coupleable to a two-dimensional display screen for generating a visual output;

a user interface processor adapted to:

obtain, from the communications module, the patient monitoring data received from each patient monitor;

control the two-dimensional display screen to provide a visual representation of the patient monitoring data generated by each patient monitor in communication with the user interface;

monitor a status of both the user interface and the display screen; and control the output module to provide a user-perceptible output indicating the status of the user interface, the plurality of patient monitors each adapted to:

generate patient monitoring data responsive to physiological data of a respective patient;

transmit the generated patient monitoring data to the user interface over a communication pathway;

monitor the status of the communication pathway between the patient monitor and the user interface; and in response to the monitored status indicating that the communication pathway, between the patient monitor and the user interface, is unable to successfully carry the patient monitoring data to the user interface, initiating transmission of the patient monitoring data to a different user interface over a different communication pathway, wherein:

the communication module is adapted to communicate with at least one other user interface, wherein the at least one other user interface is to communicate bi-directionally through encoded medical device data language messages with two or more other patient monitors;

the user interface further is adapted to use the communication module to receive patient monitoring data from the at least one other user interface regarding the two or more other patient monitors; and the user interface processor is adapted to control the two-dimensional display screen to be capable of further providing a visual representation of the patient monitoring data obtained from the at least one other user interface regarding the two or more other patient monitors.

2. The user interface of claim 1, wherein:

the communication module is further adapted to monitor a status of the communication pathways between each patient monitor and the user interface; and the user interface processor is adapted to control the output module to provide a user-perceptible output indicating the status of the communication pathways between each patient monitor and the user interface.

3. The user interface of claim 2, wherein:

the communication module is adapted to monitor a status of each communication pathway between a respective patient monitor and the user interface and/or a status of each patient monitor; and the user interface processor is adapted to control the output module to provide a user-perceptible output indicating the status of each communication pathway between a respective patient monitor and the user interface and/or each patient monitor.

4. The user interface of claim 1 wherein:

the user interface is adapted to use the communication module to transmit patient monitoring data, received from one or more patient monitors, to at least one other user interface.

5. The user interface of claim 1 wherein:

the communication module is adapted to monitor a status of a communication pathway between the user interface and each other user interface; and the user interface processor is adapted to control the output module to provide a user-perceptible output indicating the status of each communication pathway between the said user interface and each other user interface.

6. The user interface of claim 1, further comprising the two-dimensional display screen (112A).

7. The patient monitoring system of claim 1, wherein each patient monitor further comprises an audible output module, wherein the patient monitor processor is adapted to, in response to the monitored status indicating that the communication pathway, between the patient monitor and the user interface, is able to successfully carry the patient monitoring data to a user interface, stop the audible output module at the patient monitor from generating any audible outputs responsive to the patient monitoring data through the bi-directional communication.

8. The patient monitoring system of claim 1, wherein each patient monitor further comprises an audible output module, wherein the patient monitor processor is adapted to, in response to the monitored status indicating that the communication pathway, between the patient monitor and the user interface, is unable to successfully carry the patient monitoring data to a user interface, control the audible output module to provide a first audible output responsive to the patient monitoring data.

9. The patient monitoring system of claim 1, wherein each patient monitor further comprises an audible output module, wherein the patient monitor processor is adapted to, in response to the monitored status indicating that the communication pathway, between the patient monitor and the user interface, is unable to successfully carry the patient monitoring data to a user interface, control the audible output module to provide a second audible output indicating a failure of the communication pathway.

10. The patient monitoring system of claim 1, wherein each patient monitor is devoid of any two-dimensional screens for providing a visual representation of the patient monitoring data and/or is configured to be unable to communicate with a device having a two-dimensional screen over a wired communication pathway.

11. A method of controlling a user interface, comprising an output module coupleable to a two-dimensional screen, to display a visual representation of patient monitoring data generated by a plurality of patient monitors, the method comprising:

communicating bi-directionally through encoded medical device data language messages with two or more patient monitors of the plurality of patient monitors over respective communication pathways to receive, from each patient monitor, patient monitoring data generated by respective patient monitor of the plurality of patient monitors;

controlling the two-dimensional display screen of the output module to provide a visual representation of the patient monitoring data generated by each patient monitor in communication with the user interface;

monitoring a status of both the user interface and the display screen;

controlling the output module to provide a user-perceptible output indicating the status of the user interface, communicating with at least one other user interface to receive patient monitoring data obtained by the at least one other user interface, wherein the at least one other user interface is to communicate bi-directionally through encoded medical device data language messages with two or more other patient monitors;

receiving patient monitoring data from the at least one other user interface regarding the two or more other patient monitors; and controlling the two-dimensional display screen to further provide a visual representation of the patient monitoring data obtained from the at least one other user interface regarding the two or more other patient monitors;

the plurality of patient monitors each:

generating patient monitoring data responsive to physiological data of a respective patient;

transmitting the generated patient monitoring data to the user interface over a communication pathway;

monitoring the status of the communication pathway between the patient monitor and the user interface; and in response to the monitored status indicating that the communication pathway. between the patient monitor and the user interface, is unable to successfully carry the patient monitoring data to the user interface, initiating transmission of the patient monitoring data to a different user interface over a different communication pathway.

* * * * *